(12) United States Patent
Fernandez Ortega et al.

(10) Patent No.: US 9,205,128 B2
(45) Date of Patent: Dec. 8, 2015

(54) METHOD FOR INHIBITING HIV REPLICATION IN MAMMAL AND HUMAN CELLS

(75) Inventors: Celia Berta Fernandez Ortega, La Habana (CU); Anna Caridys Ramírez Suárez, La Habana (CU); Dionne Casillas Casanova, La Habana (CU); Taimi Emelia Paneque Guerrero, La Habana (CU); Raimundo Ubieta Gómez, La Habana (CU); Marta Dubed Echevarria, La Habana (CU); Leonor Margarita Navea Leyva, La Habana (CU); Lila Rosa Castellanos Serra, La Habana (CU); Carlos Antonio Duarte Cano, La Habana (CU); Viviana Falcón Cama, La Habana (CU); Osvaldo Reyes Acosta, La Habana (CU)

(73) Assignee: CENTRO DE INGENIERIA GENETICA Y BIOTECNOLOGIA, La Habana (CU)

( * ) Notice: Subject to any disclaimer, the term of this patent is extended or adjusted under 35 U.S.C. 154(b) by 0 days.

(21) Appl. No.: 13/637,845

(22) PCT Filed: Apr. 1, 2011

(86) PCT No.: PCT/CU2011/000001
§ 371 (c)(1),
(2), (4) Date: Jan. 22, 2013

(87) PCT Pub. No.: WO2011/120474
PCT Pub. Date: Oct. 6, 2011

(65) Prior Publication Data
US 2013/0130971 A1 May 23, 2013

(30) Foreign Application Priority Data
Apr. 1, 2010 (CU) .......................... 56/10

(51) Int. Cl.
| A61K 38/10 | (2006.01) |
| C12N 5/0783 | (2010.01) |
| A61K 31/713 | (2006.01) |
| A61K 31/19 | (2006.01) |
| A61K 38/17 | (2006.01) |
| A61K 45/06 | (2006.01) |
| A61K 31/7105 | (2006.01) |
| A61K 31/5575 | (2006.01) |
| C07K 14/47 | (2006.01) |
| C12N 15/113 | (2010.01) |

(52) U.S. Cl.
CPC ................ A61K 38/10 (2013.01); A61K 31/19 (2013.01); A61K 31/5575 (2013.01); A61K 31/713 (2013.01); A61K 31/7105 (2013.01); A61K 38/1709 (2013.01); A61K 38/1748 (2013.01); A61K 45/06 (2013.01); C07K 14/47 (2013.01); C07K 14/4741 (2013.01); C12N 5/0636 (2013.01); C12N 15/113 (2013.01); C12N 2310/14 (2013.01)

(58) Field of Classification Search
CPC .............. A61K 31/19; A61K 31/5575; A61K 31/7105; A61K 31/713; A61K 38/10; A61K 38/1709; A61K 38/1748; A61K 45/06; C07K 14/47; C07K 14/4741; C12N 15/113; C12N 2310/14; C12N 5/0636
See application file for complete search history.

(56) References Cited

U.S. PATENT DOCUMENTS

| 6,573,099 B2 | 6/2003 | Graham |
| 2002/0160393 A1 | 10/2002 | Symonds et al. |
| 2003/0027783 A1 | 2/2003 | Zernicka-Goetz et al. |

FOREIGN PATENT DOCUMENTS

| WO | WO 93/14778 | 8/1993 |
| WO | WO 98/00542 | 1/1998 |
| WO | WO 2009/021468 A1 | 2/2009 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*

(Continued)

*Primary Examiner* — Julie Ha
*Assistant Examiner* — Erinne Dabkowski
(74) *Attorney, Agent, or Firm* — Hoffman & Baron, LLP

(57) ABSTRACT

The present invention describes a method to inhibit replication of the human immunodeficiency virus (HIV) by negatively modulating or altering the cytoskeleton, more precisely the proteins forming the intermediate cytoskeletal filaments, wherein the said proteins are vimentin and/or keratin-10. The replication of the virus is inhibited in human cells by intervening in the structure of these proteins. The present invention is also related to the use of agents, which comprise peptides and/or interfering RNA and/or lipidic compounds, said agents producing a negative modulation or alteration of the cytoskeleton to prevent or to treat the HIV infection. The invention provides means and methods for altering the cytoskeleton/filament structure of cells, as a result of which the infection of human cells by HIV is disturbed and can even be completely inhibited. The cytoskeleton is altered by reducing the amount of vimentin and/or keratin (e.g. by transcriptional control using interfering RNA) or by using peptides that disrupt the cytoskeleton.

6 Claims, 5 Drawing Sheets

(56) References Cited

OTHER PUBLICATIONS

Bradley et al., Limits of Cooperativity in a Structurally Modular Protein: Response of the Notch Ankyrin Domain to Analogous Alanine Substitutions in Each Repeat, J. Mol. BioL (2002) 324, 373-386.*
T. V. Khakhulin, Intermediate Vimentin Filaments Involved in Type I Human Immunodeficiency Virus Replication, Academy of Sciences Reports, vol. 368, No. 5, 1999, pp. 706-708.*
UniProt Protein Database, Protein Accession Q6EIY9, Keratin, type II cytoskeletal 1, accessed on Nov. 5, 2014.*
UniProt Protein Database, Protein Accession P08670, Vimentin, accessed on Nov. 5, 2014.*
Elaine Thomas, Anti-idiotypic Antibody to the V3 Domain of gp120 Binds to Vimentin: A Possible Role of Intermediate Filaments in the Early Steps of HIV-1 Infection Cycle, Viral Immunology, vol. 9, No. 2, 1996, pp. 73-87.*
Bongaarts, John, et al., "Has the HIV Epidemic Peaked?", Population and Development Review 34 (2): pp. 199-204, Jun. 2008.
Blanco, Raquel, et al., "Cell Killing by HIV-1 Protease", Journal of Bio. Chem., vol. 278, No. 2, Issue of Jan. 10, pp. 1086-1093, 2003.
De Cock, Kevin, et al., "Preventing HIV transmission with antiretrovirals", Bulletin of the World Health Organization 2009, 87:488-488 (machine translation).
Findeis, Mark. A., et al., "Targeted delivery of DNA for gene therapy via receptors", Elsevier Science Publishers Ltd, May 1993, vol. 11, pp. 202-205.
Fernandez-Ortega C., et al., "Inhibition of in vitro HIV infection by dialysable leucocyte extracts", Kluwer Academic Publishers, Netherlands, Biotherapy 9: 33-40, 1996.
Goldman, Robert D., et al., "The Function of Intermediate Filaments in Cell Shape and Cytoskeletal Integrity", The Rockefeller University Press, The Journal of Cell Biology, vol. 134, No. 4, Aug. 1996 pp. 971-983.
Iglesias, Enrique, "Therapies and Clinical Trials with Vaccine Candidates Against HIV-1" Biotecnologia Aplicada 2009, vol. 26, No. 3., pp. 190-198.
Kalantari, Parisa, et al., "15-Deoxy-12,14-prostaglandin J2 inhibits HIV-1 transactivating protein, Tat, through covalent modification", The FASEB Journal, vol. 23, No. 8, Aug. 2009, pp. 2366-2373.
Marsden, Matthew D. et al., "Eradication of HIV: current challenges and new directions", Journal of Antimicrobial Chemotherapy, 2009, vol. 63, pp. 7-10.
Paccione, Rachel J., et al., "Keratin down-regulation in vimentin-positive cancer cells is reversible by vimentin RNA interference, which inhibits growth and motility", Molecular Cancer Therapeutics, vol. 7, No. 9, Sep. 2008, pp. 2894-2903.
Pocernich, Chava B., et al., "Proteomics analysis of human astrocytes expressing the HIV protein Tat", Molecular Brain Research, Elsevier Science BV, Amsterdam, NL, vol. 133, No. 2, Feb. 2005, pp. 307-316.
Shoeman, Robert L., et al., "Amino-terminal Polypeptides of Vimentin Are Responsible for the Changes in Nuclear Architecture Associated with Human Immunodeficiency Virus Type 1 Protease Activity in Tissue Culture Cells", Molecular Biology of the Cell, vol. 12, pp. 143-154, Jan. 2001.
Stamatakis, Konstantinos, et al., "Identification of Novel Protein Targets for Modification by 15-Deoxy-12,14-Prostaglandin J2 in Mesangial Cells Reveals Multiple Interactions with the Cytoskeleton", J. Am. Soc. Nephrol., vol. 17, No. 1, Jan. 2006, pp. 89-98.
Steinert, Peter M., "Concurrence between the Molecular Overlap Regions in Keratin Intermediate Filaments and the Locations of Keratin Mutations in Genodermatoses", Biochemical and Biophysical Research Communications, Academic Press Inc., Orlando, FL., vol. 197, No. 2, Dec. 1993, pp. 840-848.
Ui-Tei, Kumiko, et al, "Guidelines for the selection of highly effective siRNA sequences for mammalian and chick RNA interference", Oxford University Press, Nucleic Acids Research, 2004, vol. 32, No. 3, pp. 936-948.
Vallespi, Maribel G., "Identification of a novel antitumor peptide based on the screening of an Ala-library derived from the LALF32-51 region", J. Pept. Sci. 2010; vol. 16, pp. 40-47.
Wu, Rui-Yun, et al., "LIM Domain Recognition of a Tyrosine-containing Tight Turn", The Journal of Biological Chemistry, vol. 269, No. 40, Issue of Oct. 7, pp. 25085-25090, 1994.
Zhou, Xiao-Mei, et al., "The Complete Sequence of the Human Intermediate Filament Chain Keratin 10", The Journal of Biological Chemistry, vol. 263, No. 30, Issue of Oct. 25, pp. 15584-15589, 1988.
Mendez, Melissa G., et al., "Vimentin induces changes in cell shape, motility, and adhesion during the epithelial to mesenchymal transition", The FASEB Journal, vol. 24, No. 6, Jan. 22, 2010, pp. 1838-1851.
Tuschl, Thomas, et al., "Small Interfering RNAs: A Revolutionary Tool for the Analysis of Gene Function and Gene Therapy", Molecular Interventions, Jun. 2002, vol. 2, Issue 3, pp. 159-167.
Thomas, EK, et al., "Anti-idiotypic antibody to the V3 domain of gp120 binds to vimentin: a possible role of intermediate filaments in the early steps of HIV-1 infection cycle", Viral Immunology, vol. 9, No. 2, 1996, pp. 73-87. (Abstract only).

* cited by examiner

A

B

A

B

SEQUENCE LISTING

```
<160> NUMBER OF SEQ ID NOS: 12

<210> SEQ ID NO 1
<211> LENGTH: 18
<212> TYPE: PRT
<213> ORGANISM: Homo sapiens

<400> SEQUENCE: 1

Arg Val Thr Gln Met Asn Leu Asn Asp Arg Leu Ala Ser Leu Tyr Asp
1               5                   10                  15

Lys Val

<210> SEQ ID NO 2
<211> LENGTH: 18
<212> TYPE: PRT
<213> ORGANISM: Homo sapiens

<400> SEQUENCE: 2

Asp Met Glu Ile Ala Thr Tyr Arg Thr Leu Leu Glu Gly Glu Glu Ser
1               5                   10                  15

Arg Met

<210> SEQ ID NO 3
<211> LENGTH: 20
<212> TYPE: PRT
<213> ORGANISM: Homo sapiens

<400> SEQUENCE: 3

Lys Val Glu Leu Gln Glu Leu Asn Asp Arg Phe Ala Asn Tyr Ile Asp
1               5                   10                  15

Lys Val Arg Phe
            20

<210> SEQ ID NO 4
<211> LENGTH: 20
<212> TYPE: PRT
<213> ORGANISM: Homo sapiens

<400> SEQUENCE: 4

Glu Leu Asn Asp Arg Phe Ala Asn Tyr Ile Asp Lys Val Arg Phe Leu
1               5                   10                  15

Glu Gln Gln Asn
            20

<210> SEQ ID NO 5
<211> LENGTH: 20
<212> TYPE: PRT
<213> ORGANISM: Homo sapiens

<400> SEQUENCE: 5
```

```
Phe Ala Asn Tyr Ile Asp Lys Val Arg Phe Leu Glu Gln Gln Asn Lys
1               5                   10                  15

Ile Leu Leu Ala
            20
```

<210> SEQ ID NO 6
<211> LENGTH: 20
<212> TYPE: PRT
<213> ORGANISM: Homo sapiens

<400> SEQUENCE: 6

```
Asp Lys Val Arg Phe Leu Glu Gln Gln Asn Lys Ile Leu Leu Ala Glu
1               5                   10                  15

Leu Glu Gln Leu
            20
```

<210> SEQ ID NO 7
<211> LENGTH: 35
<212> TYPE: PRT
<213> ORGANISM: Homo sapiens

<400> SEQUENCE: 7

```
Lys Val Glu Leu Gln Glu Leu Asn Asp Arg Phe Ala Asn Tyr Ile Asp
1               5                   10                  15

Lys Val Arg Phe Leu Glu Gln Gln Asn Lys Ile Leu Leu Ala Glu Leu
                20                  25                  30

Glu Gln Leu
        35
```

<210> SEQ ID NO 8
<211> LENGTH: 35
<212> TYPE: PRT
<213> ORGANISM: Homo sapiens

<400> SEQUENCE: 8

```
Arg Val Thr Gln Met Asn Leu Asn Asp Arg Leu Ala Ser Leu Tyr Asp
1               5                   10                  15

Lys Val Arg Ala Leu Glu Glu Ser Asn Tyr Glu Leu Glu Gly Lys Ile
                20                  25                  30

Lys Glu Trp
        35
```

<210> SEQ ID NO 9
<211> LENGTH: 38
<212> TYPE: PRT
<213> ORGANISM: Artificial sequence
<220> FEATURE:
<223> OTHER INFORMATION: Description of the Artificial Sequence: Peptide
      derived from human keratin-10 joined to a penetrating
      peptide

<400> SEQUENCE: 9

```
Arg Val Thr Gln Met Asn Leu Asn Asp Arg Leu Ala Ser Leu Tyr Asp
1               5                   10                  15

Lys Val His Tyr Arg Ile Lys Pro Thr Phe Arg Arg Leu Lys Trp Lys
                20                  25                  30

Tyr Lys Gly Lys Phe Trp
        35
```

<210> SEQ ID NO 10
<211> LENGTH: 35

```
<212> TYPE: PRT
<213> ORGANISM: Homo sapiens

<400> SEQUENCE: 10

Ala Arg Leu Leu Cys Asp Tyr His Glu Leu Met Asn Thr Lys Leu Ala
1               5                   10                  15

Leu Asp Met Glu Ile Ala Thr Tyr Arg Thr Leu Leu Glu Gly Glu Glu
            20                  25                  30

Ser Arg Met
        35

<210> SEQ ID NO 11
<211> LENGTH: 466
<212> TYPE: PRT
<213> ORGANISM: Homo sapiens

<400> SEQUENCE: 11

Met Ser Thr Arg Ser Val Ser Ser Ser Tyr Arg Arg Met Phe Gly
1               5                   10                  15

Gly Pro Gly Thr Ala Ser Arg Pro Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
290                 295                 300
```

```
Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
            325                 330                 335

Asn Glu Ser Leu Glu Arg Gln Met Arg Glu Met Glu Glu Asn Phe Ala
        340                 345                 350

Val Glu Ala Ala Asn Tyr Gln Asp Thr Ile Gly Arg Leu Gln Asp Glu
    355                 360                 365

Ile Gln Asn Met Lys Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Ser Arg Ile Ser Leu Pro Leu Pro
            405                 410                 415

Asn Phe Ser Ser Leu Asn Leu Arg Glu Thr Asn Leu Asp Ser Leu Pro
        420                 425                 430

Leu Val Asp Thr His Ser Lys Arg Thr Leu Leu Ile Lys Thr Val Glu
    435                 440                 445

Thr Arg Asp Gly Gln Val Ile Asn Glu Thr Ser Gln His His Asp Asp
450                 455                 460

Leu Glu
465

<210> SEQ ID NO 12
<211> LENGTH: 568
<212> TYPE: PRT
<213> ORGANISM: Homo sapiens

<400> SEQUENCE: 12

Met Ser Val Arg Tyr Ser Ser Ser Lys Gln Tyr Ser Ser Ser Arg Ser
1               5                   10                  15

Gly Gly Gly Gly Gly Gly Gly Gly Ser Ser Phe Arg Ile Ser Ser
            20                  25                  30

Ser Lys Gly Ser Ile Gly Gly Phe Ser Ser Gly Gly Phe Ser Gly
        35                  40                  45

Gly Ser Phe Ser Arg Gly Ser Ser Gly Gly Gly Cys Phe Gly Gly Ser
50                  55                  60

Ser Gly Gly Tyr Gly Gly Leu Gly Gly Gly Phe Gly Gly Gly Asn Phe
65                  70                  75                  80

Gly Gly Gly Tyr Gly Ser Ser Phe Gly Gly Gly Tyr Gly Gly Val
            85                  90                  95

Ser Phe Gly Gly Gly Ser Phe Gly Gly Gly Ser Phe Gly Gly Gly Gly
        100                 105                 110

Phe Ser Gly Gly Ser Phe Gly Gly Tyr Gly Gly Tyr Gly Gly Asp
    115                 120                 125

Gly Gly Leu Leu Ser Gly Asn Glu Lys Val Thr Met Gln Asn Leu Asn
130                 135                 140

Asp Arg Leu Ala Ser Tyr Leu Asp Lys Val Arg Ala Leu Glu Glu Ser
145                 150                 155                 160

Asn Tyr Glu Leu Glu Gly Lys Ile Lys Glu Trp Tyr Glu Lys His Gly
            165                 170                 175

Asn Ser Ser Gln Arg Ala Pro Arg Asp Tyr Ser Lys Tyr Tyr Gln Thr
        180                 185                 190

Ile Glu Asp Leu Lys Asn Gln Ile Leu Asn Leu Thr Thr Asp Asn Ala
    195                 200                 205
```

```
Asn Ile Leu Leu Gln Ile Asp Asn Ala Arg Leu Ala Ala Asp Asp Phe
        210                 215                 220

Arg Leu Lys Tyr Glu Asn Glu Val Ala Leu Arg Gln Ser Val Glu Ala
225                 230                 235                 240

Asp Ile Asn Gly Leu Arg Arg Val Leu Asp Glu Leu Thr Leu Thr Lys
                245                 250                 255

Ala Asp Leu Glu Met Gln Ile Glu Ser Leu Thr Glu Glu Leu Ala Tyr
                260                 265                 270

Leu Lys Lys Asn His Glu Glu Glu Met Arg Asp Leu Gln Asn Val Ser
        275                 280                 285

Thr Gly Asp Val Asn Val Glu Met Asn Ala Ala Pro Gly Val Asp Leu
        290                 295                 300

Thr Glu Leu Leu Asn Asn Met Arg Asn Gln Tyr Glu Gln Leu Ala Glu
305                 310                 315                 320

Gln Asn Arg Lys Asp Ala Glu Ala Trp Phe Asn Glu Lys Ser Lys Glu
                325                 330                 335

Leu Thr Thr Glu Ile Asn Ser Asn Ile Glu Gln Met Ser Ser His Lys
                340                 345                 350

Ser Glu Ile Thr Glu Leu Arg Arg Thr Val Gln Gly Leu Glu Ile Glu
        355                 360                 365

Leu Gln Ser Gln Leu Ala Leu Lys Gln Ser Leu Glu Gly Ser Leu Ala
        370                 375                 380

Glu Thr Glu Gly Arg Tyr Cys Val Gln Leu Ser Gln Ile Gln Ala Gln
385                 390                 395                 400

Ile Ser Ser Leu Glu Glu Gln Leu Gln Gln Ile Arg Ala Glu Thr Glu
                405                 410                 415

Cys Gln Asn Ala Glu Tyr Gln Gln Leu Leu Asp Ile Lys Ile Arg Leu
                420                 425                 430

Glu Asn Glu Ile Gln Thr Tyr Arg Ser Leu Leu Glu Gly Glu Gly Ser
        435                 440                 445

Ser Gly Gly Gly Tyr Gly Gly Gly Arg Gly Gly Gly Ser Ser Gly
    450                 455                 460

Gly Gly Tyr Gly Gly Ser Ser Gly Gly Gly Tyr Gly Gly Ser Ser Gly
465                 470                 475                 480

Gly Gly Gly Tyr Gly Gly Gly Ser Ser Gly Gly Gly His Ile Gly
                485                 490                 495

Gly His Ser Gly Gly His Ser Gly Ser Ser Gly Gly Tyr Gly Gly
        500                 505                 510

Gly Ser Ser Ser Gly Gly Gly Tyr Gly Gly Ser Ser Gly Gly
        515                 520                 525

Gly Gly Ser His Gly Gly Ser Ser Gly Gly Gly Tyr Gly Gly Gly Ser
        530                 535                 540

Ser Ser Ser Gly Gly His Lys Ser Ser Ser Ser Gly Ser Val Gly Glu
545                 550                 555                 560

Ser Ser Ser Lys Gly Pro Arg Tyr
```

METHOD FOR INHIBITING HIV REPLICATION IN MAMMAL AND HUMAN CELLS

CLAIM OF PRIORITY

This application is the U.S. National Phase of, and Applicants claim priority from, International Application Number PCT/CU2011/000001 filed Apr. 1, 2011 and Cuban Patent Application No. 2010-0056 filed Apr. 1, 2010, which are incorporated herein by reference.

INCORPORATION OF SEQUENCE LISTING

Incorporated herein by reference in its entirety is the Sequence Listing for the above-identified Application. The Sequence Listing is disclosed on a computer-readable ASCII text file titled "SequenceListing976_79PCTUS.txt", created on Sep. 27, 2012. The sequence.txt file is 13 KB in size.

TECHNICAL FIELD

The present invention is related to the field of biomedicine, and more precisely to therapies against infections, and particularly against the infection of the human immunodeficiency virus (HIV). The present invention describes a method to inhibit HIV replication by altering the cytoskeleton, specifically those proteins forming the cytoskeletal intermediate filaments (IFs). The present invention also relates to the use of agents which negatively modulate or modify the cytoskeleton for the purpose of manufacturing drugs to prevent and to treat HIV infection.

BACKGROUND OF THE INVENTION

The emergence of the HIV/acquired immunodeficiency syndrome pandemic is among the most significant health problems arising worldwide in the last thirty years. It has led to the development of antiretroviral treatments able to stop the progression of infection and reducing mortality (De Cock K, Crowley S P, Lo Y R, Granich R M, Williams B G. *Boletin de la Organizacióon Mundial de la Salud* 2009; 87: 488-488). UNAIDS estimated in its 2008 report that there were 33 million people infected with HIV, 2.7 million of them were new cases detected in that year. It is estimated that 67% of global infections occur in sub-Saharan Africa (Report on the global AIDS epidemic 2008. Geneva, UNAIDS). According to a bulletin issued by the World Health Organization in 2009, there are two major tendencies worldwide: the total affection of the sub-Saharan African population and the concentration of infection in specific risk groups throughout the rest of the world, respectively. (De Cock K, Crowley S P, Lo Y R, Granich R M, Williams B G 2009. *Boletin de la Organización Mundial de la Salud* 87: 488-489).

The annual incidence of HIV infection peaked in the middle of the 1990's (Bongaarts J, Buettner T, Heilig G, Pelletier F. *Popul Dev Rev* 2008; 34: 199-224). However, the total number of HIV-infected people continues to increase in Africa, due to a persistently high incidence of the virus and the population growth rate (De Cock K, Crowley S P, Lo Y R, Granich R M, Williams B G 2009. *Boletin de la Organización Mundial de la Salud* 87: 488-489).

The appearance of HIV variants that are resistant against the currently available anti-HIV drugs and the poor adherence to treatment by patients remain as the main causes for therapeutic failure. Viral resistance was observed since the start of antiretroviral monotherapy, leading to the appearance of the combined anti-HIV therapy with two or more anti-HIV agents, each of them with a different mechanism of action. Morbidity and mortality rates significantly decreased among treated patients with the introduction of the highly active antiretroviral therapy (HAART). This therapy combines nucleosidic and non-nucleosidic reverse transcriptase inhibitors and protease (PR) inhibitors. Nevertheless, the multi-drug therapy does not eliminate HIV completely, with long-term treatment generally resulting in resistance to several drugs. Half of the patients receiving combined anti-HIV therapy do not completely respond to treatment, mainly due to viral resistance to one or more of the drugs applied. Additionally, viral resistance has been detected in recently infected patients, significantly limiting the therapeutic options for those patients.

The success of combined anti-HIV therapy gave an outlook on a possible eradication of the virus. However, existence of viral reservoirs has been described in latently infected cells and also in tissues where the virus persists regardless of therapy. It has been estimated that more than 70 years of continuous treatment are required to eradicate viral reservoirs, a fact considered improbable since therapy implies secondary effects and occasionally fatal metabolic complications such as lactic acidosis, diabetes mellitus, lipodystrophy, pancreatitis and others (Iglesias E 2009. *Biotecnologia Aplicada* 26: 189-194).

The adherence to HIV antiretroviral therapy is one of the most debatable issues regarding HAART, and specifically PR (protease) inhibitors, due to the fast appearance of viral resistance if the drugs are irregularly taken or the treatment is interrupted. There are several factors for non-adherence to treatment, including drug intolerance, complex administration regimes, therapeutic failure, drug interactions, social-economical problems, and others.

Combination therapy delays progression to AIDS, but does not cure the infected patients (Marsden M D, Zack J A 2009. *J Antimicrob Chemoth* 63: 7-10). Even when therapy has transformed this infection into a chronic disease rather than a fatal disease and also increased the life expectancy among patients to levels similar to those of the general population, it still represents unsolved serious problems which require the search for new strategies to decrease the used of antiretrovirals. That is the goal of the search for new therapeutic variants.

All the disadvantages of the available anti-HIV therapies support the need for new anti-HIV drugs differing mostly on their mechanisms and/or targets of action. An object of the invention is to provide a method to inhibit the replication and/or infection of the HIV. It is a further object of the invention to provide a method to inhibit the replication and/or infection of the HIV that has a different mechanism than inhibiting HIV polymerase or HIV protease. Another object of the invention is to provide a method to inhibit the replication and/or infection of the HIV by targeting the host cell and not the virus. Specifically, an object of the invention is to target the cytoskeleton, and more specifically the intermediate filaments (IFs) from the host cell. Specifically, another object of the invention is to target the host proteins vimentin and keratin-10. By targeting the host cell it is believed that it will be must more difficult for HIV to produce escape mutants. Vimentin and keratin-10 are important for the structure of the IFs and the present invention showed that they are a suitable target to inhibit HIV. Another object of the present invention is to provide agents and pharmaceutical compositions that disrupt the IFs of a cell or to decrease the amount of vimentin and/or keratin-10 host proteins.

At least one of the above mentioned objects is attained by the present invention.

SUMMARY OF THE INVENTION

The present invention is related to altering the cytoskeleton of a mammalian cell as a method to inhibit HIV replication y/o infection. The cytoskeleton is a tridimensional scaffold which contributes to the cellular integrity and plays several roles for the cell. It is formed by three main structures: microtubules, microfilaments and the intermediate filaments (IFs). The IFs comprise a set of proteins specific for each cell type, the vimentin and keratin-10 proteins among them.

Vimentin is a 58 kDa-molecular weight (MW) protein forming the IFs and commonly expressed on blood vessels endothelial cells, in certain epithelial cells and in mesenchymal cells (Alberts B, Johnson A, Lewis J, Raff M, Roberts K, Walter P 2002. Molecular Biology of the Cell, 4th ed., Garland Publishing, New York). It is known that vimentin is a substrate of the HIV PR, and it is proposed that the action of PR affects vimentin thereby could affect the cytoskeletal structure (Blanco R, Carrasco L, Ventoso I 2003. *J Biol Chem* 278: 1086-1093). It has been also demonstrated that treatment with vimentin N-terminal peptides obtained by proteolytic processing are able to rearrange the cell nucleus architecture. This nuclear architecture rearrangement is also observed in HIV-infected cells (Shoeman R L, Hüttermann C, Hartig R, Traub P 2001. *Mol Biol Cell* 12:143-154). Previous evidences suggest that HIV depends on vimentin excision for its lifecycle.

Keratins comprise a set of IFs proteins (of about 30 members) within a range of molecular weight from 10 to 68 kDa. They has been classified and numbered according to their MW and their electrophoretic behavior in acidic (pKi=4-6; type I) and neutral-basic (pKi=6-8; type II). Keratin-10 is a type-I keratin of approximately 60 kDa, found in the IFs of completely differentiated epidermal cells mainly (Zhou X M 1988. *J Biol Chem* 263: 15584-9). The present invention is directed to a method to inhibit the replication and/or infection of the HIV in a mammalian cell comprising disrupting the (structure of) cytoskeletal IFs in said mammalian cell. Furthermore the present invention is also directed to an agent that disrupts cytoskeletal IFs to prevent or to treat HIV infection.

In a first aspect, the present invention provides a method to inhibit the replication of the HIV in a mammalian cell, said method comprising disrupting or negatively modulating the (structure of) cytoskeletal IFs in a mammalian cell. In particular said mammalian cell is the target cell for infection by an HIV virus.

In a preferred embodiment of said method, the IFs comprise vimentin and/or keratin-10 proteins.

In another preferred embodiment of said method, the method comprises decreasing the amount of vimentin and/or keratin-10 in said IF to disrupt or negatively modulate the (structure of) cytoskeletal intermediate filaments and/or decreasing the amount of free vimentin and/or keratin-10 available to make new IF.

In yet another preferred embodiment of said method, the method comprises decreasing the expression of the genes encoding the vimentin and/or keratin-10 proteins to disrupt or negatively modulate the (structure of) cytoskeletal intermediate filaments.

In yet another preferred embodiment of said method, the disruption of said IF is achieved by administering to said mammalian cell a therapeutically effective dose of an agent selected from a group consisting of polypeptides, peptides, nucleic acids and chemical compounds. In one preferred embodiment, said agent is a peptide selected from the group of peptides identified as SEQ ID NOs: 1-10, and homologues thereof. In another preferred embodiment, said agent is an interfering RNA or an antisense oligonucleotide targeting vimentin and/or keratin-10 genes or their transcripts. In yet another preferred embodiment, said agent is a chemical compound or a lipidic derivative.

In another aspect, the present invention provides an agent that disrupts or negatively modulates cytoskeletal IFs to prevent or to treat HIV infection.

In a preferred embodiment of this aspect, said IFs comprise vimentin and/or keratin-10.

In another preferred embodiment of an agent according to the invention, said agent induces/achieves a decrease in the amount of vimentin and/or keratin-10 in said IFs.

In another preferred embodiment of such an agent, the agent decreases the expression of the genes encoding vimentin and/or keratin-10.

In another preferred embodiment of an agent according to the invention, said agent is selected from a group consisting of polypeptides, peptides, nucleic acids and chemical compounds.

In another preferred embodiment of an agent according to the invention, said agent comprises a peptide selected from the group of peptides identified as SEQ ID No. 1-SEQ ID No. 10, and homologues thereof.

In another preferred embodiment of an agent according to the invention, said agent is an interfering RNA or an antisense oligonucleotide, targeting vimentin and/or keratin-10 genes, or their transcripts.

In another preferred embodiment of an agent according to the invention, said agent is an interfering RNA selected from a group consisting of a siRNA, shRNA and miRNA. Preferably, said interfering RNA comprises a sequence of 15 to 50 nucleotides complementary to a region of a messenger RNA of the vimentin and/or keratin-10 proteins, preferably 18 to 25 nucleotides.

In another preferred embodiment of an agent according to the invention, said agent is a chemical compound and said compound is a lipidic compound or a lipidic derivative. Preferably said lipidic compound is prostaglandin cyclopentane 15 deoxy-$\Delta$-$^{12,14}$-PGJ2 (15d-PGJ2).

In another aspect, the present invention provides a pharmaceutical composition for treating or preventing HIV infection, said composition comprising an agent according to the present invention as described above that disrupts or negatively modulates cytoskeletal IFs according to the present invention as described above, and a pharmaceutically acceptable carrier or excipient.

In a preferred embodiment of a composition according to the invention, said agent is selected from the group consisting of polypeptides, peptides, nucleic acids and chemical compounds that disrupt IFs that comprise vimentin and/or keratin-10.

In a preferred embodiment of a composition according to the invention, said agent is a peptide selected from the group consisting of the peptides identified as SEQ ID No. 1-SEQ ID No. 10, and homologues thereof.

Preferably, said agent is an interfering RNA or an antisense oligonucleotide, targeting vimentin and/or keratin-10 genes or their transcripts.

In a highly preferred embodiment of an agent according to the invention, said agent is for use in the treatment or prevention of HIV infection, or for use in the manufacture of a medicament for the treatment or prevention of HIV infection. Treatment or prevention of HIV infection includes reference to inhibition or blockage of viral replication.

In a preferred embodiment of said pharmaceutical composition the interfering RNA is selected from a group consisting of siRNA, shRNA or miRNA.

In a preferred embodiment of said pharmaceutical composition the chemical compound is a lipidic compound or a lipidic derivative. Preferably, said lipidic compound is prostaglandin cyclopentane 15 deoxy-$\Delta$-$^{12,14}$-pGJ2.

In another aspect, the present invention provides a pharmaceutical combination comprising an agent that disrupts cytoskeletal IFs in accordance with the present invention as described herein above, and at least one anti-HIV drug. Examples of anti-HIV drugs suitable for use in aspects of the present invention include an HIV protease inhibitor, most preferably the protease inhibitor that is selected from the group consisting of: atazanavir (Reyataz™), amprenavir (Agenerase™), darunavir (Prezista™), nelfinavir (Viracept™), saquinavir (Invirase™ or Fortovase™), indinavir (Crixivan™), fosamprenavir (Lexiva™ or Telzir™), lopinavir (Aluvia™), ritonavir (Norvir™), tipranavir (Aptivus™), functional derivatives of these drugs, and combinations thereof, such as: lopinavir+ritonavir (Kaletra™). Other antiretroviral drugs that can be used in aspects of the present invention are non-nucleoside reverse transcriptase inhibitors (nNRTI) such as: efavirenz (Stocrin™) and nevirapine (Viramune™), etravirine (Intelence™), rilpivirine (TMC-278), loviride (R89439), delavirdine (Rescriptor™), functional derivatives of these drugs and combinations thereof. Other antiretroviral drugs that can be used in aspects of the present invention are nucleoside reverse transcriptase inhibitors (NRTIs) or nucleoside analogue reverse transcriptase inhibitors (NARTIs) such as: lamivudine (3TC or Epivir™), abacavir (Ziagen™), zidovudine (AZT or Retrovir AZT™), stavudine (d4T or Zerit™), zalcitabine (ddC or Hivid™), didanosine (ddI or Videx™) emtricitabine (FTC or Emtriva™), tenofovir (Viread™), apricitabine (AVX754), stampidine, elvucitabine (L-Fd4C), racivir, amdoxovir, functional derivatives of these drugs, and combinations thereof, such as: emtricitabine+tenofovir (Truvada™), zidovudine+lamivudine (Combivir™), and abacavir+lamivudine+zidovudine (Trizivir™).

In addition to the above-mentioned antiretroviral drugs, the pharmaceutical combination of the present invention may comprise combinations of various classes of antiretroviral drugs listed above, such as the combinations: efavirenz+zidovudine+lamivudine, efavirenz+tenofovir+emtricitabine, lopinavir boosted with ritonavir+zidovudine+lamivudine, and lopinavir boosted with ritonavir+tenofovir+emtricitabine.

In a preferred embodiment of a pharmaceutical combination according to the invention the agents and drugs are administered simultaneously, separately or sequentially, as part of a dosage regime.

In another aspect, the present invention provides a method of treating or preventing HIV infection in subject in need thereof, comprising administering to said subject a therapeutically effective dose of a pharmaceutical composition.

DETAILED DESCRIPTION OF THE INVENTION

Figure 1:
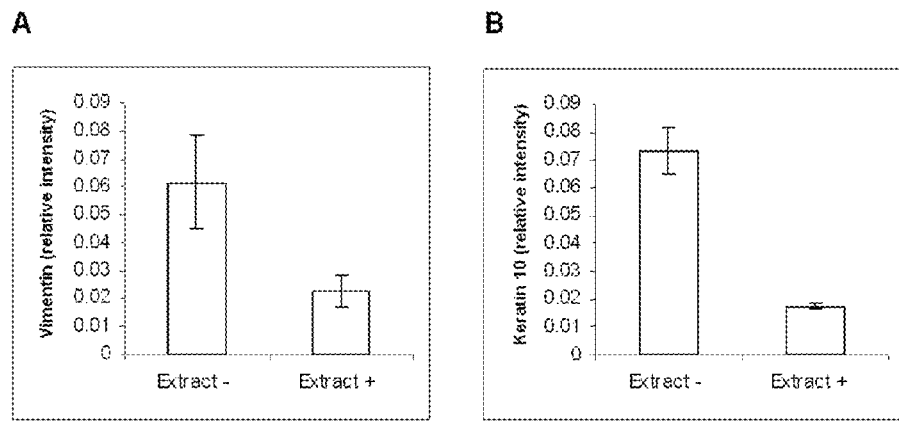
FIG. 1. Relative intensity of the human vimentin and keratin-10 proteins as identified by comparative proteomics. Panel A shows the decrease of vimentin protein in the cultures treated with an anti-HIV activity-bearing extract. Panel B shows the decrease of the keratin-10 protein in cultures treated with the anti-HIV activity-bearing extract. Error bars stand for standard deviations.

The present invention solves the problem mentioned above, and describes a method to inhibit the HIV replication by disrupting the cytoskeleton, more precisely the proteins forming cytoskeletal IF.

For the purpose of the invention, said IF can be composed by acidic keratin, basic keratin, vimentin, desmin, glial fibrillary acidic factor, peripherin, neurofilament (NF) protein, internexin, filensin, phakinin, and lamin.

In an embodiment of the invention, said IF can be composed by vimentin and keratin proteins. More particularly, said IF can be formed by the vimentin and keratin-10 proteins. The altered cytoskeleton inhibits the HIV viral replication in human cells.

By disrupting the cytoskeletal IFs is meant that the structure of the IFs is modified or altered in such a way that down regulate the proteins forming cytoskeletal IF and/or structural breakage of cytoskeletal IF in shorter subunits and/or change the structural form of the cytoskeletal network and/or that the IF are disassembled. Cytoskeleton as described herein refers to cellular "scaffolding" or "skeleton" contained within the cytoplasm and is made out of protein. The cytoskeleton is present in all cells; it plays important roles in both intracellular transport and cellular division. It is formed by three main structures: microtubules, microfilaments and the intermediate filaments (IFs). The cytoskeleton provides the cell with structure and shape. Cytoskeletal elements interact extensively and intimately with cellular membranes.

The IFs as defined herein are a family of related proteins that share common structural and sequence features. Intermediate filaments have an average diameter of 10 nanometers, which is between that of actin (microfilaments) and microtubules. Most types of intermediate filaments are cytoplasmatic, but one type, the lamins, are nuclear. There are about 70 different genes coding for various intermediate filament proteins, specific for each cell type, the vimentin and keratin-10 proteins among them.

The term "vimentin", as used herein, refers to the member of the intermediate filament family of proteins identified by NCBI Reference Sequence: NP_003371.2, having the sequence as given in SEQ ID NO. 11. Vimentin proteins form filamentous polymers in a series of assembly steps starting from antiparallels, half-staggered double dimmers (or tetramers) to form unit-length filaments (ULF) that are assembled longitudinally to form the complete filament.

The term "keratin", as used herein, refers to the family of fibrous structural proteins or intermediate filaments. Keratin proteins form filamentous polymers in a series of assembly steps beginning with dimerization; dimers assemble into tetramers and octamers and eventually into ULF capable of annealing end-to-end into long filaments. Each type I keratin is coexpressed with a specific type II keratin partner, and each keratin pair that is formed as coassembly of a specific preferred and predetermined pairs is characteristic and indicative of differentiation and specialization of a particular type of epithelial cell.

The term "keratin-10", as used herein, refers to Keratin, type I cytoskeletal 10, the member of the intermediate filament family of proteins identified by Swiss-Prot accession number: Q6E1Z0.1, having the sequence as given in SEQ ID NO: 12.

The term "gene", as used herein refers to a DNA sequence including but not limited to a DNA sequence that can be transcribed into mRNA which can be translated into polypeptide chains, transcribed into rRNA or tRNA or serve as recognition sites for enzymes and other proteins involved in DNA replication, transcription and regulation.

The term refers to any DNA sequence comprising several operably linked DNA fragments such as a promoter region, a 5' untranslated region (the 5' UTR), a coding region (which may or may not code for a protein), and an untranslated 3' region (3'UTR) comprising a polyadenylation site. Typically, the 5'UTR, the coding region and the 3'UTR are transcribed into an RNA of which, in the case of a protein encoding gene, the coding region is translated into a protein. The gene usually comprises introns and exons.

The term "vimentin gene", as used herein, refers to the gene encoding the protein vimentin or a homologue thereof.

The term "keratin-10 gene", as used herein, refers to the gene encoding the protein keratin-10 or a homologue thereof.

The term "disrupting" as used herein with reference to disruption of the intermediate filaments as indicated herein refers to interference with function or structural organization. In particular, disruption may involve structural breakage, inhibition of polymerization, inhibition of formation and biosynthesis, including inhibition of formation of primary, secondary and tertiary protein structures, etc.

The term "negatively modulating" as used herein with reference to negatively modulating the intermediate filaments as indicated herein, refers to changing or altering function or structural organization in a manner that results in loss or decreasing of biological function of said filaments.

The term "cytoskeletal intermediate filaments (IFs)" as used herein, refers to Intermediate filaments as a type of cytoskeletal elements, and their size is intermediate compared with actin and microtubules. Together these three enhance the structural integrity, cell shape, and cell and organelle motility. Cytoskeletal intermediate filaments are regularly devided into five types: Types I and II: Acidic Keratin and Basic Keratin. Keratins also have subtypes that are unique to different epithelial cells; Type III: Vimentin in fibroblasts, endothelial cells and leukocytes; desmin in muscle; glial fibrillary acidic factor in astrocytes and other types of glia, and peripherin in peripheral nerve fibers; Type IV Neurofilament (NF) proteins H (heavy), M (medium) and L (low), internexin filensin and phakinin; and Type V: Lamins.

The term "structure of cytoskeletal intermediate filaments (IFs)" as used herein, refers to the helical organization of tetramers of the filaments. Each intermediate filament monomer consists of an alpha helical rod domain which connects the amino (head) and carboxyl (tail) terminals. The rods coil around another filament to form a dimer. The N and C terminals of each filament are aligned. Some Intermediate filaments form homodimers; other form heterodimers. The dimers then form staggered tetramers that line up head-tail. This tetramer is considered the basic subunit of the intermediate filament. The final intermediate filament is a helical array of these tetramers.

In the context of this specification, the terms "treatment" and "treating" refer to any and all uses which remedy a condition or disease or symptoms thereof, prevent the establishment of a condition or disease or symptoms thereof, or otherwise prevent or hinder or reverse the progression of a condition or disease or other undesirable symptoms in any way whatsoever.

The term "therapeutically effective dose", as used herein refers to a non-toxic amount of the therapeutic agent sufficient to provide the desired therapeutic effect, e.g. to treat, ameliorate, or prevent a desired disease or condition, or to exhibit a detectable therapeutic or preventative effect. The effect can be detected by, for example, chemical markers or antigen levels. Therapeutic effects also include reduction in physical symptoms. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician.

For purposes of the present invention, an effective dose will be from about 0.01 mg/kg to 50 mg/kg or 0.05 mg/kg to about 10 mg/kg of the polynucleotide or polypeptide compositions in the individual to which it is administered.

The term "pharmaceutically acceptable carrier or excipient", as used herein refers to a carrier for administration of a therapeutic agent, such as a polypeptide, polynucleotide, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991). Typically, the therapeutic compositions are prepared as injectables, either as liquid solutions or suspensions, or in solid forms, either suitable for solution in, or suspension in, liquid vehicles or for direct intake. Liposomes are included within the definition of a pharmaceutically acceptable carrier, as are arosols.

The term "homologue" as used herein, and when referring to a peptide refers to a the peptide comprising an amino acid sequence sharing at least a 70% sequence identity as established by sequence alignment with e.g. Blast etc, preferably at least 75%, more preferably at least 85%, 90% or even 95%, most preferably at least 97%, sequence identity with SEQ ID No. 1 to SEQ ID No. 10 sequences, and with the ability to disrupt, negatively modulate or modify the cytoskeleton, specifically the proteins forming the cytoskeletal IFs and more precisely the vimentin and keratin-10 proteins. Suitable homologues are peptides with conservative amino acid substitutions. Suitable less than 10% of the amino acids are substituted, more suitable less than 5%, less than 3% and most preferably less than 1% of the amino acids are substituted. Suitable less than 10 amino acid residues are substituted, more suitably less than 5, and most suitably less than 2 amino acids are substituted. A conservative substitution is one in which an amino acid is replaced by another very similar amino acid, which substitution has little or no effect on the activity of the protein. A "conservative substitution" is the replacement of an amino acid with another amino acid that has the same net electronic charge and approximately the same size and shape. Amino acids with aliphatic or substituted aliphatic amino acid sidechains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution: Group I: glycine, alanine, valine, leucine, isoleucine, serine, threonine, cysteine, and non-naturally occurring amino acids with C1 C4 aliphatic or C1 C4 hydroxyl substituted aliphatic sidechains (straight chained or monobranched). Group II: glutamic acid, aspartic acid and non-naturally occurring amino acids with carboxylic acid substituted C1 C4 aliphatic side chains (unbranched or one branch point). Group III: lysine, ornithine, arginine and non-naturally occurring amino acids with amine or guanidine substituted C1 C4 aliphatic side chains (unbranched or one branch point). Group IV: glutamine, asparagine and non-naturally occurring amino acids with amide substituted C1 C4 aliphatic side chains (unbranched or one branch point). Group V: phenylalanine, phenylglycine, tyrosine and tryptophan.

The term "% sequence identity" is defined herein as the percentage of nucleotides in a nucleic acid sequence that is identical with the nucleotides in a nucleic acid sequence of interest, after aligning the sequences and optionally introducing gaps, if necessary, to achieve the maximum percent sequence identity. Methods and computer programs for alignments are well known in the art. As used herein, the terms "nucleic acid sequence" and "nucleotides" also encompass non-natural molecules based on and/or derived from nucleic acid sequences, such as for instance artificially modified nucleic acid sequences, peptide nucleic acids, as well as nucleic acid sequences comprising at least one modified nucleotide and/or non-natural nucleotide such as for instance inosine.

The term "RNA interference", refers to the process where an interfering RNA (iRNA) causes intracellular degradation of specific mRNA and can be used to interfere with the translation of a desired mRNA target.

The term "interfering RNA" refers to a double or simple stranded RNA (iRNA) agent, by which is meant a small nucleic acid molecule used for RNA interference. Short iRNA agents that are about 15-30 nucleotides in length are referred to as "small-interfering RNA" or "siRNA." Longer iRNA agents are generally referred to as "double-stranded RNA" or "dsRNA", other forms of iRNA agents are microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like. A DNA molecule that transcribes dsRNA or siRNA (for instance, as a hairpin duplex) also provides RNA interference. DNA molecules for transcribing dsRNA are disclosed in U.S. Pat. No. 6,573,099, and in U.S. Patent Publication Nos. 20020160393 and 20030027783. DNA molecules for transcribing siRNA are reviewed in Tuschl and Borkhardt, Molecular Interventions, 2:158 (2002).

The term "antisense RNA" as used herein, refers to any RNA that binds to mRNA with enough affinity to decrease the amount of protein translated from the mRNA. The amount of protein translated from the mRNA is preferably decreased by more than 20%; more preferably decreased by more than 50%, 70%, and 80%; and most preferably decreased by more than 90%. Antisense RNA materials and methods are well known in the art.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein.

By the term "inhibiting the expression" is meant silencing or downregulation of a gene or nucleic acid which refers to a detectable decrease of transcription and/or translation of a target nucleic acid sequence, i.e., the sequence targeted by the iRNA, or a decrease in the amount or activity of the target sequence or protein in comparison to the normal level that is detected in the absence of the interfering RNA or other nucleic acid sequence. A detectable decrease can be as small as about 5% or 10%, or as great as about 80%, 90% or 100%. More typically, a detectable decrease is about 20%, 30%, 40%, 50%, 60%, or 70%.

The term "lipidic compound" as used herein, refers to fatty acid analogues derived from e.g. monounsaturated fatty acids, polyunsaturated fatty acids and lipids comprising 1-6 triple bonds.

"HIV" is the retrovirus Human Immunodeficiency Virus, a virus that causes immunodeficiency by attacking CD4+ cells in the body. The term "HIV", as used herein, includes any HIV, including all groups and subtypes (clades) of HIV-1 and HIV-2, for example HIV-1 M and HIV-1 O groups; the invention embraces each of the known clades; HIV-1 is preferred.

The term "replication" as used herein, refers to the process in which a complementary strand of a nucleic acid molecule is synthesized by a polymerase enzyme. In the particular context of the present invention, the term replication as used herein in reference to a virus, refers to the completion of a complete or entire viral life cycle, wherein infectious viral particles or virions attach to the surface of the host cell (usually binding to a specific cell surface molecule that accounts for the specificity of the infection). Once inside the cell, the virions are uncoated and viral genes begin to express proteins needed for replication of the genome and synthesis of new proteins to make new capsids and cores leading to the assembly of progeny infectious virus particles which, themselves, are capable of infecting and replicating in new host cells. Thus, a viral life cycle is only complete if within a single cell, infection by one or more virus particles or virions proceeds all the way to the production of fully infectious progeny virus particles. In the particular case of retroviruses, a complete viral life cycle involves infectious viral particles containing the viral RNA entering a cell, the RNA being reverse transcribed into DNA, the DNA being integrated into the host chromosome as a provirus, and the infected cell producing virion proteins and assembling them with full length viral genomic RNA into new, equally infectious particles.

The term "host cell" as used herein, refers to a cell used for the expression of a viral genome, or propagation of a vector or virus.

The term "CD4+ cells" as used herein, refers to a major classification of T lymphocytes, referring to those that carry the CD4 antigen.

In particular, the present invention refers to methods negatively modulating, modifying or disrupting the cytoskeletal IFs. Preferred IFs contain vimentin and/or keratin-10 proteins. In a preferred embodiment, the method comprises decreasing the amount of vimentin and/or keratin-10 in the IFs. The decrease of vimentin and or keratin-10 may be affected in several ways. A preferred embodiment is decreasing or inhibiting coding genes expression for vimentin and/or keratin-10. More preferably, the expression levels of vimentin and/or keratin-10 in the IFs is decreased or the structure of the cytoskeletal vimentin and/or keratin-10- is altered. The structure of cytoskeleton IFs may be altered by modifying the structure of the IF proteins, e.g. by cleavage or misfolding, preferably the structure of vimentin and/or keratin-10.

The evidences referred in the technical literature suggest that HIV requires vimentin excision during its lifecycle. Surprisingly, in the present invention, viral replication is inhibited through what seems to be a natural mechanism present during viral infection. It is not obvious to try to disrupt the cytoskeleton and/or take away vimentin as a means to inhibit HIV infection, in fact one would expect that the infection would be much faster, as the disruption of the cytoskeleton also happens during normal infection.

The applicants identified vimentin and keratin-10 cytoskeletal proteins by a comparative proteomic analysis of MT4 cells treated with a fraction of a human leukocyte extract showing anti-HIV activity. It was found that leukocyte extract having anti-HIV activity showed a decrease and/or destabilization of vimentin and/or keratin-10 and/or the IFs. Previously, Thomas et al. demonstrated that an anti-vimentin antibody was able to block the binding of the HIV-1 gp120 glycoprotein to the cell surface vimentin, preventing the cell entry of the virus (Thomas E K, Connelly R J, Pennathur S, Dubrousky L, Haffar O K, Bukrinsky M I 1996. *Viral Immunol* 9: 73-87). Surprisingly, very low inhibition levels of viral replication were detected under the experimental conditions tested for the present invention, by using an antibody against vimentin (aimed to decrease the HIV infection). Thomas et al. used an antibody against vimentin thus blocking vimentin that is accessible to the antibody. This is very different from the action proposed in the present invention. In the present invention, vimentin is altered and/or decreased so to disrupt the IFs. By blocking the vimentin as done in Thomas et al. the IFs are not altered. The experimental data also confirms the difference mode of action in methods of the present invention. Very high percent of inhibition of viral replication, up to 100%, were obtained when vimentin levels are decreased and/or vimentin structure destabilized in the target cell, as observed in the Example 2, FIGS. 3 and 4, while in Thomas et al. a maxium of 47% of inhibition was observed.

Figure 3:
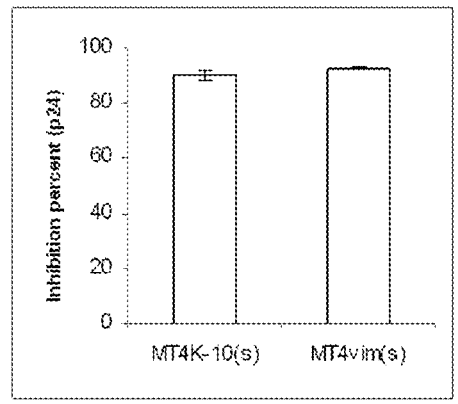
FIG. 3. Inhibition of HIV-1 replication in MT4$_{vim(s)}$ and MT4$_{k-10(s)}$ cell cultures as evaluated by assessing the p24 antigen. MT4, MT4$_{vim(s)}$ and MT4$_{k-10(s)}$ cell cultures were challenged with the HIV-1 strain Bru, at a multiplicity of infection (m.o.i.) of 0.01. Viral replication was inhibited in more than 90% in MT4$_{vim(s)}$ and MT4$_{k-10(s)}$ cell cultures. Error bars stand for standard deviations.
Figure 4:
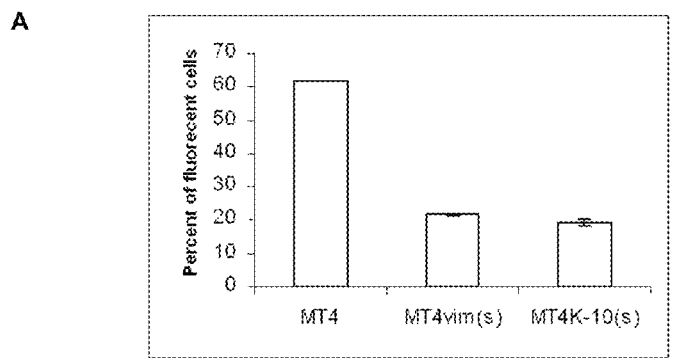
FIG. 4. Challenge assay with the pLGW lentiviral vector in MT4, MT4$_{vim(s)}$ and MT4$_{K-10(s)}$ cell cultures. Cultured cells were transduced with a lentiviral vector which resembles the first stages of the HIV-1 viral replication cycle after entry, also carrying the GFP reporter gene. A) MT4$_{vim(s)}$ and MT4$_{k-10(s)}$ cell cultures showing a decreased percent of fluorescent cells once transduced with the lentivirus, compared to the unsilenced MT4 cells. Error bars stand for standard deviation. B) Flow cytometry histograms of each culture.
Figure 4:
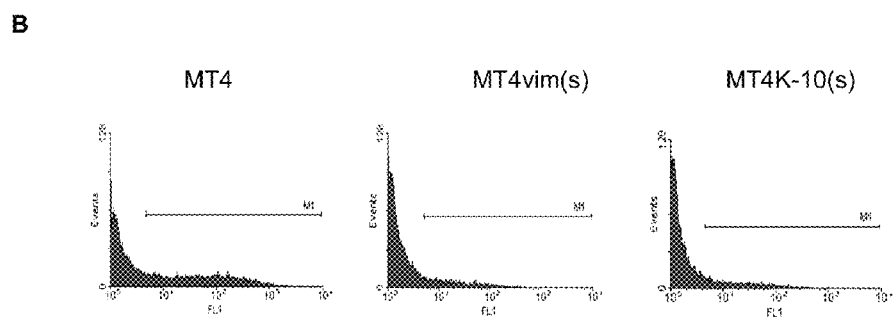

Moreover, there are no reports on the binding of keratin-10 to the viral gp120 protein and, precisely, HIV replication was also inhibited by inhibiting and/or destabilizing keratin-10, as shown in Example 2, FIGS. 3 and 4.

To further gain insight of the mechanism of HIV replication inhibition, an experimental system was used which cellular entry is not mediated by the gp120 viral protein. That system comprises an HIV-1 based non-replicating lentiviral vector that is devoid of gp120 and also expressing the green fluorescent protein (GFP). As shown in Example 2, there was an efficient "infection" of MT4 cells by this lentivirus, and the cultures showed high percent of GFP expression indicative of an efficient penetration of the cell and integration into the cellular genome of this lentiviral vector. In this HIV-1-based lentiviral "infection" system, a decrease of vimentin generates a dramatic decrease in the lentiviral "infection", as shown in Example 2. This demonstrates that the method used in the present invention to inhibit HIV-1 infection is not related to the binding of gp120 to vimentin as proposed by Thomas et al. Hence, this invention is related to a method not previously reported for inhibiting HIV infection.

Furthermore we demonstrated with the aid of transmission electron microscopy (TEM) that IFs are destabilized in MT4 cells silenced for vimentin ($MT4_{vim(s)}$), as well as in cells silenced for keratin-10 ($MT4_{K-10(s)}$, resulting in a inhibited "infection" of the HIV-1-based lentiviral vector (Example 3). $MT4_{vim(s)}$ and $MT4_{K-10(s)}$ cells were obtained by means of introducing RNA hairpins specific for each of the protein coding genes.

The disruption of the IFs may be achieved by an agent selected from a group consisting of polypeptides, peptides, nucleic acids and chemical compounds. In a preferred embodiment the agent is a peptide, more preferably the peptide is a peptide selected from the group consisting of peptides identified as SEQ ID No. 1 to SEQ ID No. 10, and homologues thereof.

In another preferred embodiment the agent is an interfering RNA or an antisense oligonucleotide targeting vimentin and/or keratin-10 genes.

In another preferred embodiment the agent is a chemical compound or a lipidic derivative. A suitable lipidic compound is said lipidic compound is prostaglandin cyclopentane 15 deoxy-$\Delta$-$^{12,14}$-PGJ2.

The present invention describes methods to treat and/or prevent the infection of human cells by HIV. Those methods involve the disruption of IFs and in particular the disruption of vimentin and/or keratin-10 in the cell, in order to prevent or treat the HIV infection in the cell.

The negative regulation occurs within an HIV host cell of a given subject, for the means of preventing or inhibiting the effective infection of the host cells of the subject. Thus, the present invention similarly comprises methods to treat and/or to prevent the infection of a subject with HIV.

The inhibition of infection with HIV by using the method described in the present invention is applied both at cellular level and for the whole organism. The term inhibition implies complete or partial inhibition of the infection.

The present invention describes the manipulation of IFs and in particular vimentin and/or keratin-10 cytoskeletal proteins to inhibit HIV replication. This strategy provides the advantage of minimal or inexistent viral resistance over the antiretroviral drugs currently available, since these proteins are endogenous cellular proteins rather than viral. The mechanisms of action of the drugs of the present invention operate through pathways different to those already described and showing a high inhibition capacity. Therefore, its combination with drugs currently available against the HIV infection could enhance the effectiveness of anti-HIV treatments. Moreover, the use of the therapeutic agents of the present invention could be combined with the novel therapeutic strategies already proposed in the state of the art, as the transplantation of stem cells bearing modified endogenous genes. The therapeutic modality of the present invention provides a new option for those patients showing multiple drug resistance, who represent a high percent among the patients treated with the currently available therapy.

In spite of a possible damage of the IFs structure leading to toxicity or even cellular death, a surprising major achievement of this invention comprises inhibiting the HIV infection without affecting cellular viability, all these adding even more novelty for the treatment of patients infected with HIV.

The present invention also comprises the use of agents that negatively modulate, modify, or disrupt the cytoskeleton, more precisely the proteins forming the cytoskeletal IFs and specifically vimentin and/or keratin-10, to produce a pharmaceutical to prevent or to treat the HIV infection. Such agents can be fused and/or conjugated to other molecules. Such agents include peptide-like compounds, interfering RNA and lipidic compounds producing the negative modulation or modifying the cytoskeleton, IFs, and particularly those agents negatively modulating vimentin and/or keratin-10.

Vimentin and/or keratin-10 can be negatively modulated by putting the cell into contact with the agent that negatively modulates vimentin and/or keratin-10. The agent can be formulated to increase its capacity for cell penetration as required. The negative modulation can be achieved by administering an agent to a subject, such agent negatively modulating vimentin and/or keratin-10 in the cells of the subject. The agent is administered in such a way that it is contacted with the cells of the subject, which are already infected with HIV or which could be potentially infected. Such cells are referred herein as HIV host cells. The administration of the agent comprises the agent getting into contact with the host cell. Administration routes include the parenteral route and those by which the agent is delivered through the mucosae of the subject. In a specific embodiment of aspects of the invention, the host cell is a CD4+ cell.

In an embodiment of the invention, the negative modulation or modification can be achieved by directly affecting vimentin and/or keratin-10, either by reducing the expression of the gene or protein synthesis, by modifying the structure of the filaments formed by these proteins, by destabilizing filament structure or reducing its activity/function.

Within the context of the present invention, negative modulation (or modification) comprises the inhibition of the level of vimentin and/or keratin-10 proteins in the cell, or modification, destabilization, disassembly or even destruction of the structure of the IFs containing these proteins within the cell.

Any agent known as inhibiting or negatively modulating IFs and in particular vimentin and/or keratin-10 can be used to inhibit the HIV infection, according to the method explained in the present invention.

Similarly, the HIV infection can also be inhibited by using peptide- or polypeptide-like agents that negatively modulate or destabilize IFs and in particular vimentin and/or keratin-10. Such agents comprise endogenous proteins or proteins that are not normally present within the host cell. They could be, for example, mutated proteins, genetically engineered proteins, peptides, synthetic peptides, recombinant proteins, chimeric proteins, antibody fragments, humanized proteins, humanized antibodies, chimeric antibodies, modified proteins and fragments of all of them.

In the present invention, the use of peptides capable of disrupting the structure of IFs, in particular those which contain vimentin and/or keratin-10, was found to strongly inhibited the infection of MT4 cells with HIV, corroborating the results obtained in $MT4_{vim(s)}$ and $MT4_{K-10(s)}$ cells. This supports the use of those peptides to prevent or to treat the HIV infection, as part of the present invention.

In a preferred embodiment of aspects of the invention, the peptides are those identified in the sequence listing as SEQ ID No. 1 to SEQ ID No. 10. The invention also comprises the use of homologues of those peptides. The peptides can be fused to another molecule, for example, can be fused to a penetrating peptide.

An agent useful to prevent or to treat the HIV, according to the present invention, is that agent able to inhibit the expression of vimentin and/or keratin-10 genes, or its protein synthesis, or the structure of IFs which contain vimentin and/or keratin-10. A preferred agent, according to the present invention, comprises an agent that silences the vimentin and/or keratin-10 genes or transcripts thereof by using an iRNA, such as a small interfering RNA (siRNA), a short hairpin RNA (shRNA) or a micro RNA (miRNA).

RNA interference refers to a type of selective posttranscriptional gene silencing process which destroys the specific messenger RNA (mRNA) by means of a molecule which binds and inhibits the mRNA processing. For example, it can inhibit translation of the mRNA or degrade it. Within the context of the present invention, iRNA refers to any type of interfering RNA, including, but not restrained to, a siRNA, shRNA, endogenous miRNA and an artificial miRNA.

The term siRNA used herein refers to a nucleic acid forming a double strand of RNA which is able to reduce or inhibit the expression of the vimentin and/or keratin-10 genes. The siRNA sequence can correspond to the entire sequence of the vimentin and/or keratin-10 genes. The typical siRNA is at least 15 to 50 nucleotides long, preferentially being 19 to 30 nucleotides long. A siRNA can be chemically synthesized, produced by in vitro transcription or be produced within a cell which is specifically used to produce it.

The term shRNA is used herein as a type of siRNA. These shRNA are made up of a short antisense strand of, for example, 19 to 25 nucleotides and followed by a loop of 5 to 9 nucleotides and the analogous sense strand. Alternatively, the sense strand can precede the nucleotide loop and the following antisense strand. shRNAs function as siRNA and/or siRNA species, but they differ in that shRNAs show particular hairpin-like structures for increased stability. These shRNAs as other agents described herein, can be delivered as plasmids, retroviruses and lentiviruses and be expressed from promoters such as the U6 polimerase III promoter or others.

Delivery methods for the interfering RNA type agents to the target cell can include, for example, the injection of a composition containing the agent, or the said composition getting into direct contact with the cell, for example, a hematopoietic cell getting into contact with a composition containing the interfering RNA. In another case, the interfering RNA type agent can be directly injected by any route for direct inoculation into the bloodstream, such as a venous or arterial route, for example, by hydrodynamic injection or catheterization. In some cases, the interfering RNA agent can be delivered to specific organs or systemically. The colloidal dispersion systems can be used as delivery vehicles to increase the in vivo stability of the agents.

The agents may inhibit the expression of the vimentin and/or keratin-10 genes through mechanisms similar to those used by, for example, an oligonucleotide or a nucleic acid analogue. They include, for example, a peptide-nucleic acid (PNA), a pseudo complementary PNA (pc-PNA), locked nucleic acids (LNA) and their derivatives. The nucleic acid sequences code for proteins which act as transcriptional repressors, antisense molecules, ribozymes, small inhibitory nucleic acid sequences such as interfering RNA, shRNA, siRNA, miRNA and antisense oligonucleotides.

The agents can resemble the shape of any entity normally present or not, at the levels being administered to the cell or the organism. Agents such as chemicals, small molecules, aptamers, can be identified or generated to negatively modulate IFs and in particular vimentin and/or keratin-10. Within the context of the present invention, aptamers are single-stranded nucleic acids showing well defined tridimensional structures to facilitate its binding to target molecules in a manner conceptually similar to that of antibodies. Aptamers combine the optimal properties of both small molecules and antibodies, including their high specificity and affinity, chemical stability, low immunogenicity and the capacity to attack protein-protein interactions. The agent can function directly as administered, but it could be also modified or used intracellularly to generate the negative modulation of vimentin and/or keratin-10. For example, the introduction of a nucleic acid sequence into the cell and its transcription results in the production of the nucleic acid and/or the protein which inhibits IFs protein and in particular vimentin and/or keratin-10 within the cell.

The agent may comprise a vector. Vectors can be episomal, for example, plasmids, vectors derived from viruses such as cytomegaloviruses, adenoviruses, etc., or can be integrated into the genome of the target cell, for example, vectors derived from retroviruses such as the Moloney Murine Leukemia Virus, HIV-1, the avian leukosis virus, and others. Vectors based on HIV or the Feline Leukemia Virus can be used to transfect non-dividing cells. Vectors combining different retroviruses can be used.

Several viral and virus-associated vectors have being described in the state of the art. Such vectors can be used as carriers for transferring a nucleic acid construct to the cell. The constructs can be integrated in non-replicative viral genomes similar to adenoviruses (adeno-associated viruses, AAV), herpes simplex viruses, or others, including retroviral and lentiviral vectors to infect or transduce the cells. An HIV-based vector can be particularly useful in HIV host cells.

Another embodiment of the present invention comprises a pharmaceutical composition comprising the agent according to the present invention. The agents mentioned in the present invention and contained within the said composition can be combined to each other or be associated to other therapeutic agents such as, but not limited to, the already known anti-HIV drugs (for example, zidovudine (AZT).

In a preferred embodiment the negative modulation of IFs and in particular vimentin and/or keratin-10 is applied in the present invention to cells able to be infected by the HIV, for the purpose of preventing or reducing the infection of HIV in that cell. In a preferred embodiment, the human cell is a CD4+ cell. The application of such negative modulation to a whole organism, a human or a primate, may be an effective therapeutic treatment for the organism against HIV infection.

Another embodiment of the present invention is a pharmaceutical combination comprising an agent according to the present invention and a anti-HIV drug. In the pharmaceutical combination, the agents and drugs being part of it can be administered simultaneously, separately or sequentially.

Advantages of the Invention

The present invention is advantageous over the currently available antiretroviral drugs because it avoids viral resistance or reduces its probabilities for occurrence to the minimum. This is based on the cellular endogenous rather than viral origin of IFs and in particular vimentin and keratin-10 proteins.

The drugs of the present invention act with a high inhibition capacity through mechanisms different to those already described in the prior art. Therefore, its combination with currently available therapeutic drugs specific for the HIV infection could enhance the effectiveness of anti-HIV treatments.

On the other hand, the use of the therapeutic agents of the present invention could be combined with novel therapeutic alternatives proposed in the state of the art, such as transplantation of stem cells bearing endogenous modified genes.

The present invention offers a new therapy to patients resistant to multiple drugs, which represent a high percent among patients treated with the currently available therapy.

Delivery Methods

Once formulated, the pharmaceutical compositions of the invention can be (1) administered directly to the subject; (2)

delivered ex vivo, to cells derived from the subject; or (3) delivered in vitro for expression of recombinant proteins.

Direct delivery of the compositions will generally be accomplished by injection, either subcutaneously, intraperitoneally, intravenously or intramuscularly, or delivered to the interstitial space of a tissue. The compositions can also be administered into the nervous system. Other modes of administration include topical, oral, suppositories, and transdermal applications, needles, and particle guns or hyposprays. Dosage treatment may be a single dose schedule or a multiple dose schedule.

Methods for the ex vivo delivery and re-implantation of transformed cells into a subject are known in the art and described in e.g., International Publication No. WO 93/14778. Examples of cells useful in ex vivo applications include, for example, stem cells, particularly hematopoietic, lymph cells, macrophages, dendritic cells, or tumor cells.

Generally, delivery of nucleic acids for both ex vivo and in vitro applications can be accomplished by, for example, dextran-mediated transfection, calcium phosphate precipitation, polybrene mediated transfection, electroporation, encapsulation of the polynucleotide(s) in liposomes, and direct microinjection of the DNA, all well known in the art. Methods for introducing polynucleotides (such as siRNAs) into a cell are known in the art. Methods for introducing nucleic acid for instance comprise calcium phosphate transfection, DEAE-Dextran, electroporation or liposome-mediated transfection. Alternatively, direct injection of the polynucleotide is employed. Preferably however, a nucleic acid sequence is introduced into a cell by a vector, preferably a viral vector. Said vector preferably comprises a retroviral, adenoviral, adeno-associated viral (AAV), or lentiviral vector.

Various methods are used to administer the therapeutic composition directly to a specific site in the body. Receptor-mediated targeted delivery of therapeutic compositions containing an antisense polynucleotide, subgenomic polynucleotides, or antibodies to specific tissues is also used. Receptor-mediated DNA delivery techniques are described in, for example, Findeis et al., Trends in Biotechnol. (1993) 11:202-205; Wu et al., J. Biol. Chem. (1994) 269:542-46.

Pharmaceutical compositions containing polynucleotides are preferably administered in a range of about 100 ng to about 200 mg of polynucleotides for local administration in a gene therapy protocol. Concentration ranges of about 500 ng to about 50 mg, about 1 µg to about 2 mg, about 5 µg to about 500 µg, and about 20 µg to about 100 µg of polynucleotides can also be used during a gene therapy protocol. Factors such as mode of action and efficacy of transformation and expression are considerations which will affect the dosage required for ultimate efficacy of the polynucleotides. Where greater expression is desired over a larger area of tissue, larger amounts of polynucleotides or the same amounts re-administered in a successive protocol of administrations, or several administrations to different adjacent or close tissue portions of, for example, a nerve ending or synaps, may be required to affect a positive therapeutic outcome. In all cases, routine experimentation in clinical trials will determine specific ranges for optimal therapeutic effect. A more complete description of gene therapy vectors, especially retroviral vectors, is contained in WO 98/00542.

EXAMPLES

Example 1

Comparative Proteomics of MT4 Cells Treated with a Leukocyte Extract Showing Anti-HIV Activity The MT4 cell line was treated with a leukocyte extract showing anti-HIV activity (Fernandez-Ortega C; Dubed M; Ruibal I; Vilarrubia O L; Menéndez JC; Navea L et al. 1996, *Biotherapy* 9: 33-40) and the resulting protein expression profile was compared to a control of untreated cells. The cells were lysed and centrifuged at 12 000 rpm for 20 min. The supernatant was collected and the pellet was subjected to a second lysis procedure. After a second centrifugation step under the same conditions, the second supernatant was collected together with the first one, being further delipidated with ethyl alcohol and alkylated with polyacrylamide. Afterwards, the deoxyribonucleic acid (DNA) was precipitated and a bidimensional electrophoresis of the sample was carried out by using a 12.5 to 3% Tris-Tricine polyacrylamide gel at 4° C.

The images of analytical gels were analyzed by using the Melanie 5 software. Spots to be identified were cut out from the preparative gels and further digested with trypsin. The proteolytic peptides were extracted for mass spectrometry analysis and mass spectra were obtained by using a hybrid mass spectrometer with QTOF-2 orthogonal geometry and equipped with a nanospray ionization source.

ESI-MS/MS spectra were analyzed, and the respective searches were carried out for protein identification in the non-redundant protein sequence database of the National Center for Biotechnology Information of the USA and in the European Molecular Biology Laboratory database of Germany. A decrease in cytoskeletal proteins was detected in the sample treated with the anti-HIV leukocyte extract, particularly in those forming the IFs (vimentin and keratin-10) (FIG. 1).

Example 2

Interfering RNA Against Vimentin and Keratin-10 Inhibits HIV Infection

Figure 2:
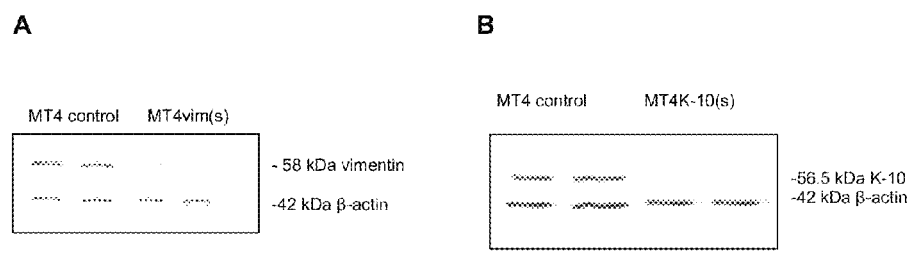
FIG. 2. Detection of vimentin and keratin-10 proteins in cultures stably silenced for each of both proteins. Vimentin (A) and keratin-10 (B) were assessed by western blot in the MT4 cell line subjected to silencing for each protein, MT4$_{vim(s)}$ and MT4$_{K-10(s)}$ respectively. MT4$_{vim(s)}$ and MT4$_{K-10(s)}$ cultures showed a decreased expression of the respective protein compared to the MT4 cell culture. The β-actin protein was used as control to normalize the western blot analysis. Each variant was analyzed in duplicate lanes. In this figure, K-10 stands for keratin-10.

The MT4 cell line was transduced by using the pLenti-shRNA$_{vim}$ or pLenti-shRNA$_{K-10}$ lentiviral vectors, which bear a sequence encoding a RNA hairpin which silences the expression of the vimentin and keratin proteins, respectively. These lentiviral vectors were assembled by packaging in the 293T cell line transduced with four plasmids. The said plasmids were pLP1, pLP2, pLP/VSVG and p-shRNA, this last specific for either vimentin or keratin-10. The pLP1 vector codes for the gene products of the gag/pol sequences of HIV-1. The pLP/VSVG codes for the surface protein of the vesicular stomatitis virus and the p-shRNA contains the genome of the lentiviral vector which bears the sequences coding for the vimentin- or keratin-10-specific RNA hairpins (Ui-Tei K, Naito Y, Takahashi F, Haraguchi T et al., 2004 *Nucleic Acids Research* 32: 936-948; Santa Cruz Biotechnology). All the plasmids were amplified in the *Escherichia coli* XL-1 strain under ampicillin selection. The four plasmid vectors were transfection-quality purified by column chromatography and put together into contact with the 293T packaging cell line in the presence of polyethyleneimine. The cells were incubated for 48 h at 37° C. under 5% $CO_2$ atmosphere, and virions were further purified by ultracentrifugation at 20 000×g. Once purified the lentiviral vector, MT4 cells were transduced and the recombinants were selected for blasticidin resistance. The recombinant clones were isolated by the limiting dilution assay and cultivated in RPMI medium supplemented at 10% with fetal bovine serum (FBS) under 5% $CO_2$ atmosphere and 95% relative humidity at 37° C. until harvest. Total proteins were extracted from the cultures and silencing of vimentin was demonstrated by western blot in MT4 (MT4$_{vim(s)}$) cells, as well as for keratin-10 in the MT4$_{K-10(s)}$ cells silenced for keratin-10. Transduced cultures showed a decreased expression of vimentin or keratin-10 compared to the MT4 untransduced control, respectively (FIG. 2).

The anti-HIV activity was evaluated in two challenge systems:

System A: Cells stably silenced for the vimentin (MT4$_{vim(s)}$) or keratin-10 (MT4$_{K-10(s)}$ proteins were cultured in RPMI medium supplemented at 10% FBS under a 5% $CO_2$ atmosphere and relative humidity of 95% at 37° C. The challenge with total virus was carried out in MT4$_{vim(s)}$, MT4$_{K-10(s)}$ and MT4 cell cultures. The Bru viral strain was used at m.o.i. of 0.01, and replication was evaluated by determining the p24 antigen concentration in culture supernatants by the ELISA method. The MT4$_{vim(s)}$ and MT4$_{K-10(s)}$ cells showed approximately a 90% inhibition of viral replication compared to the MT4 cell cultures unsilenced for each of these proteins (FIG. 3).

System B: The MT4$_{vim(s)}$, MT4$_{K-10(s)}$ and MT4 cell cultures were challenged with a lentiviral vector bearing part of the HIV-1 genome, lacking the genes involved in infectivity and entry (pLGW). This vector was constructed by packaging the products of four plasmids in the 293T cell line. The said plasmids were pLP1, pLP2, pLP/VSVG and pLGFP, this last coding for the GFP. The pLP1 plasmid codes for the gene products of the HIV-1 gag/pol sequences. The pLP2 plasmid bears the genetic sequence of the HIV-1 Rev protein and the pLP/VSVG codes for the surface protein of the vesicular stomatitis virus. The pLGFP plasmid codes for the GFP, also bearing the packaging sequence, the HIV Rev-responsive element sequences (RRE) and also the 3"-deleted HIV-1 long terminal repeats (LTRs), constituting the lentiviral vector genome. GFP expression was followed as marker of completing the viral replication cycle after entry and until integration. The results were followed by fluorescence microscopy, and the number of fluorescent cells decreased in the MT4$_{vim(s)}$ and MT4$_{K-10(s)}$ cultures, compared to that on MT4 cell cultures (data not shown). The samples were analyzed by flow cytometry and the number of fluorescent cells because of GFP expression decreased nearly 70% as compared to the unsilenced MT4 cell cultures (FIG. 4).

Example 3

Changes in the Structure of Intermediate Filaments in MT4 Cells

Figure 5:
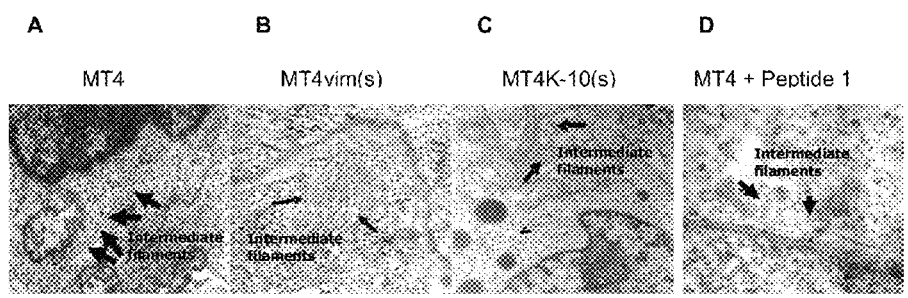
FIG. 5. IFs structural analysis in MT4 cell cultures. MT4, MT4$_{vim(s)}$ and MT4$_{K-10(s)}$ cell cultures were analyzed by transmission electron microscopy. Silenced cultures (B, C) showed shortened IFs, instead of the long filaments observed in unsilenced MT4 cell cultures used as control (A). Panel D shows fragmented IFs by the action of the peptide identified as SEQ ID No. 1 on MT4 cells.

Firstly, MT4$_{vim(s)}$, MT4$_{K-10(s)}$ and MT4 cells were fixed in 3.2% glutaraldehyde for 1 h at 4° C. and then fixed in 2% osmium tetroxide for 1 h at 4° C. They were subsequently washed with 0.1 M phosphate buffered saline (PBS), pH 7.2, and dehydrated at increasing ethanol concentrations (30, 50, 70 and 100%) for 10 min each at 4° C. Inclusion was carried out and ultrathin 40-50 nm-width sections were taken in an ultramicrotome (NOVA, LKB), which were placed on 400-orifices nickel trays. Once the ultrathin cuts were taken and placed on the trays, they were contrasted with saturated uranyl acetate and lead citrate, and further examined under a JEOL JEM 2000 EX (JEOL) microscope. Five microphotographs were analyzed at different magnifications. MT4 cell intact IFs are shown in FIG. 5A, meanwhile these structures appeared shortened in MT4$_{vim(s)}$ MT4$_{K-10(s)}$ cells (FIGS. 5B and C, respectively). Section D shows that effect in IFs as caused by the action of a peptide (peptide identified as SEQ ID No. 1) which disassembles the structure of vimentin in MT4 cells. Inhibition of the viral replication was observed under these conditions. Vimentin or keratin-10 proteins were identified at IFs by immunomicroscopy.

Example 4

Synthetic Peptides which Inhibit HIV Replication in MT4 Cells

Figure 6:
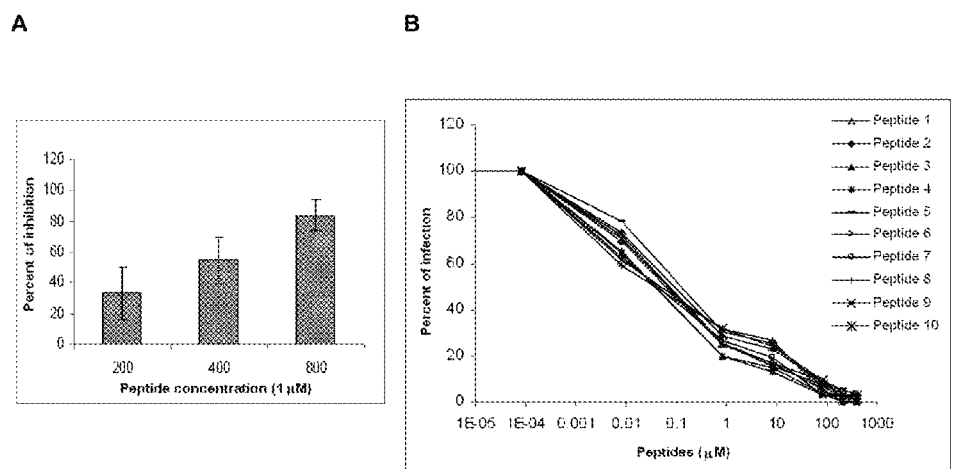
FIG. 6. Inhibition of HIV-1 replication in MT4 cells by peptides. A) Cells were incubated with the peptide for 24 h and further challenged with the HXB1 HIV-1 strain at m.o.i. of 0.05. Viral replication was inhibited at high percents, which also increased together with peptide concentration. Error bars stand for standard deviation. B) Cells were incubated with peptides for 24 h and further incubated with the HIV Bru strain at m.o.i. of 0.01. The inhibitory concentration 50 (IC50) was at the nanomolar level for all the peptides.

Peptides corresponding to amino acid sequences of the human keratin-10, human keratin 1 and human vimentin were synthesized (Goldman R D, Khuon S, Hao Chou Y, Opal P, Steinert P M 1996, *J Cell Biol* 134: 971-983; Steinert P M, Yang J M, Bale S J, Compton J G 1993, *BBRC* 197: 840-848). One of the peptides has a cell penetrating peptide conjugated at its C terminus (Vallespi M G, Fernandez J R, Torrens I, Garcia I; Garay H, Mendoza O et al. 2009. *J Peptide Science* 16: 40-47). The anti-HIV activity of said peptides was evaluated by using a total virus challenge system, in the presence of different viral strains: HXB1 (HIV-1 IIIB clone) and Bru. The MT4 cell line was incubated with the peptide for 24 h prior to viral challenge. The assays were done at m.o.i. values of 0.01 and 0.05, comprising nine replicas for each experimental variant. The value of the p24 viral antigen was determined in cell cultures by using an ELISA type assay, and results were expressed as percent of viral inhibition or as percent of infection, both versus peptide concentration. An important inhibition of viral replication was observed in the presence of peptides, both when the cultures were challenged at a high viral concentration (SEQ ID No. 1, FIG. 6A) and at a m.o.i. of 0.01 (FIG. 6B). The IC50 of peptides was in the nanomolar range.

Example 5

Figure 7:
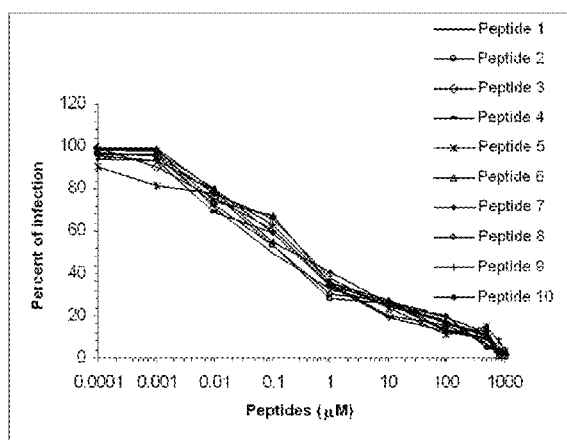
FIG. 7. Inhibition of HIV-1 replication by the different peptides in peripheral blood mononuclear cells (PBMCs). These cells were pre-stimulated, treated with different concentrations of the peptides and further infected with the HIV-1 Bru strain. The peptides inhibited HIV replication in a dose-dependent manner.

Synthetic Peptides which Inhibit HIV Replication in Peripheral Blood Mononuclear Cells PBMCs were isolated from whole blood of healthy individuals by cesium chloride Ficoll density gradients. Cells were pre-stimulated for 2 days in RPMI medium supplemented at 20% FBS, 100 U/mL Interleukin 2 (IL-2) and 5 µg/mL phytohemagglutinin (PHA). Subsequently, they were kept in PHA-free medium and seeded at 150 000 cells per well in 96-well plates. After 24 h, the peptides were added at the different concentrations and the cultures infected with the HIV-1 Bru strain at a m.o.i. of 0.01. The cultures were kept for 7 days, with the medium being changed and peptides added every 3 days. The cultures were harvested and the supernatants collected to evaluate the presence of the p24 viral protein. The peptides inhibited the HIV-1 replication in a dose-dependent manner (FIG. 7). Similar IC50 results in the nanomolar range were obtained in cultures infected with the HIV-1 BaL1 strain.

Example 6

Inhibition of HIV-2 by Synthetic Peptides

Figure 8:
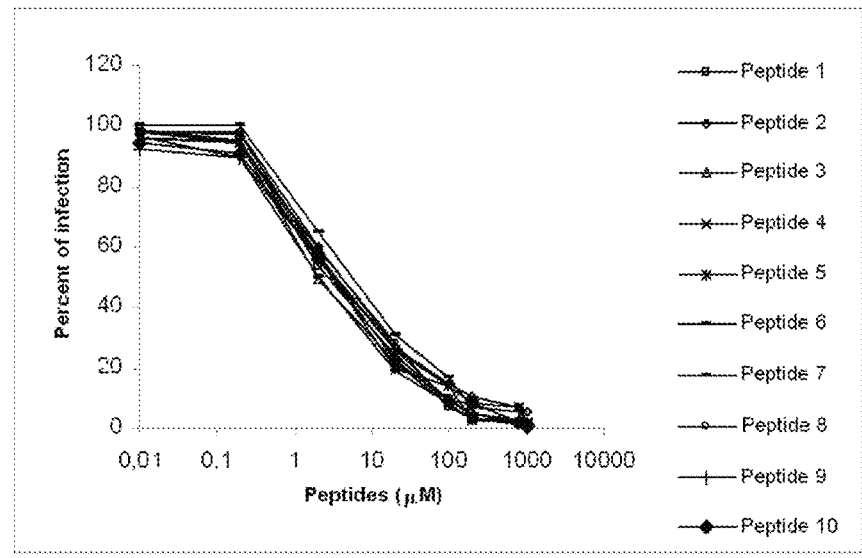
FIG. 8. Inhibition of HIV-2 replication by the peptide identified as SEQ ID No. 1, 2, 3, 4, 5, 6, 7, 8, 9 y 10. PBMCs were pre-stimulated, treated with the different concentration of the peptides and further infected with the HIV-2 CBL-20 strain. The peptides inhibited HIV-2 replication in a dose-dependent manner.

PBMCs were isolated from whole blood of healthy individuals by using Ficoll density gradients. The cells were pre-stimulated for 2 days with RPMI medium supplemented at 20% FBS, 100 U/mL IL-2 and 5 µg/mL PHA. Cells were subsequently maintained in PHA-free medium and seeded at 150 000 cells per well in 96-well plates. After 24 h, peptides were added at different concentrations and the cultures were infected with the CBL-20 HIV-2 strain. The cultures were kept for 7 days, being changed every 3 days the medium and the peptides added. Cultures were harvested and supernatants collected to evaluate the presence of the p24 viral protein. The peptides inhibited the HIV-2 replication in a dose-dependent manner (FIG. 8).

Example 7

Decrease of Vimentin in the Presence of Peptides Identified as SEQ ID No. 1, 4, 5, 7, 8 and 9

Figure 9:
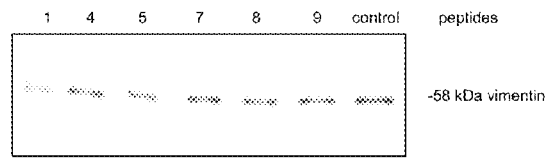
FIG. 9. Decreased vimentin in the presence of the peptides identified as SEQ ID No. 1, 4, 5, 7, 8 and 9. The MT4 cell line was incubated with said peptides at 50 μM each for 24 h. Vimentin was detected by the western blot technique. Vimentin bands showed a decreased intensity in the cultures treated with the peptides.

The MT4 cell line was incubated at 50 µM of each peptide for 24 h. The vimentin protein was detected by the western blot technique. Cellular extracts were resuspended in 1% sodium dodecyl sulphate (SDS) and applied in a 10% polyacrylamide gel, being further transferred to a Hybond-P cellulose membrane. For immunoidentification purposes, anti-vimentin and anti-β actin (as control) antibodies were used. An anti-mouse IgG antibody-peroxidase conjugate was used as secondary antibody. The activity of the peroxidase enzyme was visualized by using diaminobenzidine in the presence of hydrogen peroxide and PBS. The vimentin protein was decreased in MT4 cells treated with the peptides (FIG. 9).

Example 8

Cellular Penetration of Peptides Identified as SEQ ID No. 1 and SEQ ID No. 3

Figure 10:
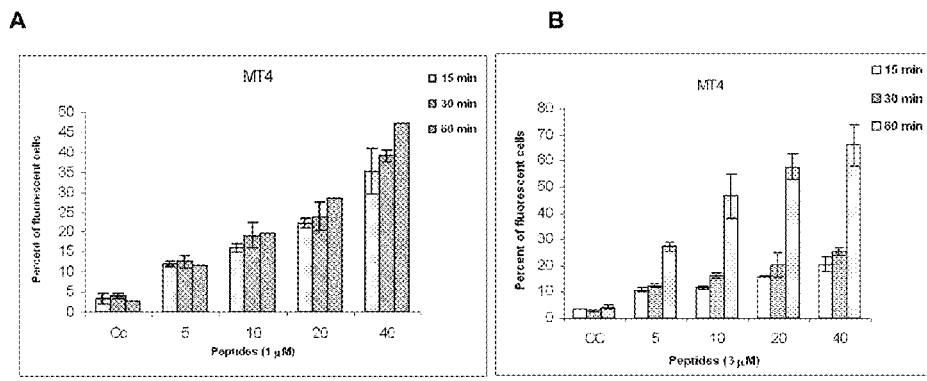
FIG. 10. Assessment of internalization of the peptides identified as SEQ ID No. 1 (A) and SEQ ID No. 3 (B) in the MT4 cell line. The graph represents the percent of fluorescent cells corresponding to peptide penetration at 5, 10, 20 and 40 μM concentrations and at different time points in the MT4 cell line. Cc: Untreated cells. Error bars stand for standard deviations.

HeLa CD4+ cells were seeded in RPMI medium supplemented at 10% FBS and incubated until reaching 60% confluence of the monolayer. MT4 cells were seeded at 50 000 cells per well in RPMI medium at 10% FBS. Peptides identified as SEQ ID No. 1 and SEQ ID No. 3 were resuspended in injection water and evaluated at 5, 10, and 40 µM concentrations. Peptides were incubated for 24 h at 37° C. under a 5% $CO_2$ atmosphere, and penetration was evaluated after 15, 30 and 60 min. After each period of time, cells were harvested and immediately analyzed by flow cytometry. Three replicates were analyzed per experimental variant. The peptides were able to penetrate by their own into the MT4 cells as shown in FIG. 10.

Example 9

Lipidic Derivative which Binds to Vimentin and Inhibits HIV-1 Replication

Figure 11:
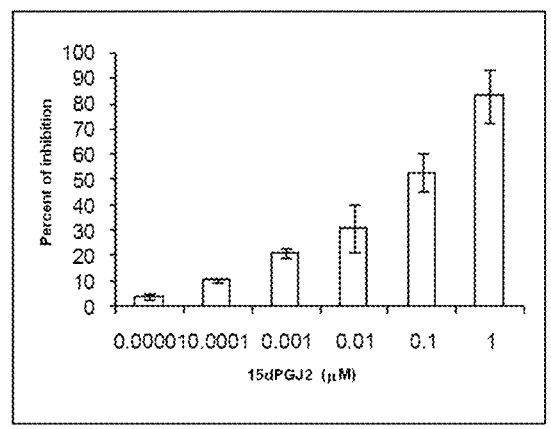
FIG. 11. Inhibition of HIV-1 replication by a lipidic derivative. MT4 cells were incubated with different concentrations of the prostaglandin cyclopentane 15 deoxy-$\Delta$-$^{12,14}$-PGJ2 (15d-PGJ2), and further challenged with the HIV-1 (Bru strain) at m.o.i. of 0.01. The 15d-PGJ2 prostaglandin inhibited the HIV-1 replication. Error bars represent standard deviations.

It is known that the prostaglandin cyclopentane 15 deoxy-$\Delta^{-12,14}$-PGJ2 (15d-PGJ2) binds to the vimentin protein (Stamatakis K, Sánchez-Gómez FJ, Pérez-Sala D 2006, *J Am Soc Nephrol* 17: 89-98). In the present invention, it was demonstrated that 15d-PGJ2 inhibits the HIV replication in vitro. The antiviral activity assay was carried out on MT4 cells challenged with HIV-1 (Bru strain). The cells were incubated at different concentrations of 15d-PGJ2, and further challenged with HIV-1 at a m.o.i. of 0.01. After a 5-day incubation period, cell cultures were harvested and the p24 protein was evaluated in the supernatants (FIG. 11).

Example 10

Effect of Synthetic Peptides and 15d-PGJ2 on PBMCs of HIV-1 Infected Patients

PBMCs were isolated from whole blood of HIV-1 infected individuals by Ficoll density gradients. Cells were pre-stimulated and treated with the peptides, similarly as described in example 5, or treated with 5 µM of 15d-PGJ2. Replication was evaluated by determining the p24 antigen concentration on culture supernatants by the ELISA method. The p24 values significantly decreased in PBMCs treated with the peptides or with the lipidic derivative, compared to untreated cells (Table 1). This was indicative of the inhibition of HIV-1 replication caused by treatment with these compounds.

TABLE 1

Percent of HIV-1 inhibition in PBMCs of infected individuals, which were treated ex vivo with the peptides or 15d-PGJ2.

| Compound | % of HIV-1 inhibition |
| --- | --- |
| Peptide 1 (SEQ ID No. 1) | 89.3 |
| Peptide 2 (SEQ ID No. 2) | 81.1 |
| Peptide 3 (SEQ ID No. 3) | 85.3 |
| Peptide 4 (SEQ ID No. 4) | 84.9 |
| Peptide 5 (SEQ ID No. 5) | 82.1 |
| Peptide 6 (SEQ ID No. 6) | 80.5 |
| Peptide 7 (SEQ ID No. 7) | 83.7 |
| Peptide 8 (SEQ ID No. 8) | 86.7 |
| Peptide 9 (SEQ ID No. 9) | 81.3 |
| Peptide 10 (SEQ ID No. 10) | 83.4 |
| 15d-PGJ2 | 80.1 |

IFs structure was analyzed by transmission electron microscopy, following the methodology described in Example 3. It was shown that IFs were very short in those infected individuals PBMCs which were treated with the peptides or with the lipidic derivative, as compared to untreated cells.

Example 11

Interfering RNA Against Vimentin and Keratin-10 Inhibits HIV in PBMCs of Infected Individuals PBMCs were isolated from whole blood of HIV-1 infected individuals by Ficoll density gradient. Cells were pre-stimulated for 2 days in RPMI medium at 20% FBS, 100 U/mL IL-2 and 5 µg/mL PHA. Subsequently, they were kept in PHA-free medium and further transduced with the lentiviral vectors pLenti-shRNA$_{vim}$ or pLenti-shRNA$_{K-10}$, which bear a sequence coding for a RNA hairpin to silence the vimentin and the keratin-10 proteins, respectively. Vectors were obtained as described in Example 2. Replication was evaluated by determining the concentrations of the p24 antigen on culture supernatants by the ELISA method. PBMCs silenced for the vimentin or keratin-10 proteins showed a high inhibition of viral replication as compared to the cultures unsilenced for each of these proteins (Table 2).

TABLE 2

Percent of HIV-1 inhibition in PBMCs from infected individuals, which were transduced with shRNA specific for vimentin or keratin-10

| PBMCs from infected individuals | % of HIV-1 inhibition |
| --- | --- |
| PBMCs transduced with pLenti-shRNA$_{vim}$ | 89.5 |
| PBMCs transduced with pLenti-shRNA$_{K-10}$ | 75.6 |

IFs structures were analyzed by transmission electron microscopy, following the methodology described in Example 3. It was shown that IFs structure was shorter in those PBMCs from infected individuals which were transduced with the lentiviral vectors, as compared to untransduced cells.

Example 12

Treatment of HIV-1 Infected Patients with Formulations Containing the Peptides Identified as SEQ ID No. 1 and 2

Eight HIV-1 seropositive patients having less than a year from diagnosis and values of CD4+ T cells higher than 350 cells/mm$^3$ were treated with a formulation containing the peptide identified as SEQ ID No. 1 or a formulation containing the peptide identified as SEQ ID No. 2. The peptides were administered at 150 mg per day, and patients were followed up for 6 months attending to viral load and CD4+ T cell counts. The viral load was undetectable in two of the patients after treatment, and decreased in more than 1.5 log in the other six patients. On the other hand, seven patients registered an increase in CD4+ T cells higher than 50 cells/mm$^3$, while the CD4+ T cell counts decreased in the other patient. The IFs structure was analyzed by transmission electron microscopy according to the methodology described in Example 3, in two of the patients treated with the peptide identified as SEQ ID No. 1 and three of the patients treated with SEQ ID No. 2. IFs appeared shortened in all the cases.

---

The invention claimed is:

1. A method to inhibit the replication of the human immunodeficiency virus (HIV) comprising disrupting the structure of cytoskeletal intermediate filaments (IFs) in a mammalian cell, wherein said disruption of IFs is achieved by administering to a human subject in need thereof a peptide selected from the group consisting of SEQ ID NO: 1 to SEQ ID NO: 10 and homologues thereof, said homologues having at least 85% sequence identity with any one of SEQ ID NO: 1 to SEQ ID NO: 10 and having the ability to disrupt, negatively modulate or modify the cytoskeletal IFs in said mammalian cell.

2. The method according to claim 1 wherein said IFs comprise vimentin and/or keratin proteins.

3. The method according to claim 2 wherein said IFs comprise vimentin and/or keratin-10 proteins.

4. The method according to claim 1 wherein the administering of the peptide decreases the amount of vimentin and/or keratin-10 in said IFs.

5. The method according to claim 1 wherein the administering of the peptide decreases the expression of the genes coding for vimentin and/or keratin-10.

6. A method of treating HIV infection in a mammal in need thereof, comprising administering to said mammal a therapeutically effective dose of a pharmaceutical composition, said composition comprising a peptide selected from the group consisting of SEQ ID NO: 1 to SEQ ID NO: 10 and homologues thereof, said homologues having at least 85% sequence identity with any one of SEQ ID NO: 1 to SEQ ID NO: 10 and having the ability to disrupt, negatively modulate or modify the cytoskeletal IFs in cells of said mammal.

* * * * *